United States Patent [19]

Furihata

[11] 4,409,993
[45] Oct. 18, 1983

[54] ENDOSCOPE APPARATUS

[75] Inventor: Hiroyuki Furihata, Hamura, Japan

[73] Assignee: Olympus Optical Co., Ltd., Tokyo, Japan

[21] Appl. No.: 283,520

[22] Filed: Jul. 15, 1981

[30] Foreign Application Priority Data

Jul. 23, 1980 [JP] Japan ................. 55-100884

[51] Int. Cl.³ .......................... A61B 1/06; A61N 5/04
[52] U.S. Cl. .................... 128/784; 128/303.1; 128/399; 128/401; 128/804
[58] Field of Search ...................... 128/3–11, 128/303.1, 303.11–303.12, 348, 349 R, 399, 401, 783–784, 786, 788, 804, 303.15

[56] References Cited

U.S. PATENT DOCUMENTS

| | | | |
|---|---|---|---|
| 3,294,085 | 12/1966 | Wallace | 128/303.15 |
| 3,610,231 | 10/1971 | Takahashi et al. | 128/6 |
| 3,858,577 | 1/1975 | Bass et al. | 128/8 |
| 3,886,944 | 6/1975 | Jamshidi | 128/303.1 |
| 4,072,147 | 2/1978 | Hett | 128/6 |
| 4,154,246 | 5/1979 | Le Veen | 128/784 |
| 4,176,662 | 12/1979 | Frazer | 128/6 |
| 4,190,053 | 2/1980 | Sterzer | 128/399 |
| 4,197,860 | 4/1980 | Sterzer | 128/804 |
| 4,204,549 | 5/1980 | Paglione | 128/784 |
| 4,233,493 | 11/1980 | Nath | 128/303.1 X |
| 4,292,960 | 10/1981 | Paglione | 128/804 |
| 4,311,154 | 1/1982 | Sterzer et al. | 128/804 |
| 4,312,364 | 1/1982 | Convert et al. | 128/804 |

FOREIGN PATENT DOCUMENTS 2417263 10/1975 Fed. Rep. of Germany ...... 128/804
1188490 4/1970 United Kingdom ................ 128/804

OTHER PUBLICATIONS

Mendecki et al., "Microwave-Induced Hyperthermia in Cancer Treatment," Int. J. Radiation Oncology Biol. Phys., vol. 4, No. 11-12, Nov.-Dec., 1978, pp. 1095-1103.

Primary Examiner—Lee S. Cohen
Assistant Examiner—Angela D. Sykes
Attorney, Agent, or Firm—Frishauf, Holtz, Goodman and Woodward

[57] ABSTRACT

An endoscope apparatus, wherein a microwave irradiator is provided in an endoscope distal end portion. The microwave irradiator includes a pole type antenna and a parabolic reflector which surrounds the antenna and has a parabolic plane. The antenna is directly connected to one end of a microwave-transmitting wire, and the other end of the microwave-transmitting wire is connected to a microwave oscillator of a microwave-generating device by means of a connector. When the endoscope distal end portion is inserted into a coeliac cavity of a patient, medical treatment microwaves having a prescribed radiation energy are conducted to the microwave irradiator through the microwave-transmitting wire. Microwaves emitted from the irradiator are projected on an affected coeliac tissue of a patient to be medically treated, for example, that in which a tumor is grown.

20 Claims, 6 Drawing Figures

ENDOSCOPE APPARATUS

BACKGROUND OF THE INVENTION

This invention relates to an endoscope apparatus which is provided with a microwave irradiator to treat an affected coeliac tissue of a living body such as a cancerous tumor by emitting microwaves to the affected portion.

A known effective medical treatment of a tumor grown in a living body is based on thermal extermination. With a conventional endoscope apparatus applying this medical treatment process, hot air or water is ejected on a tumor from an outlet port provided at the distal end portion of the endoscope. When contacted by ejected hot air or water, the tumor perishes. Later, the hot air or water is recovered into the endoscope body through an inlet also formed at the distal end portion of the endoscope.

Where a tumor is exposed on the surface of a living tissue, the conventional endoscope arranged as described above enables the tumor to be medically treated with good effect. However, a normal living tissue is maintained at a prescribed coeliac temperature by a self-adjusting system, that is, blood circulation through the tissue. Where, therefore, a tumor happens to be grown under the normal tissue, then the hot air or water can not reach the interior of the living tissue where the tumor is produced, resulting in the failure to effectively treat a tumor in a living tissue due to the fact that proper heating of the tumor is not possible.

It may be contemplated to apply an endoscope type high frequency knife or endoscope type laser knife to thermally excise an affected, for example, tumor-contaminated tissue. However, these devices are originally developed to surgically excise the affected coeliac portion of a living body, and generally irradiate extremely high energy. Where, therefore, the high frequency or laser output is irradiated on a normal tissue by mistake, then the danger arises of unnecessarily damaging or exterminating a normal tissue. Consequently, the endoscope type high frequency knife or laser knife is not practically applicable for thermal medical treatment of an affected portion of a deep coeliac section.

SUMMARY OF THE INVENTION

It is accordingly the object of this invention to provide an endoscope apparatus which is provided with a microwave oscillator and assures the safe and reliable medical treatment of an affected tissue grown on and in a living coeliac tissue.

To attain the above-mentioned object, this invention provides an endoscope apparatus which comprises an endoscope provided with a control section and insertion section drawn into a coeliac cavity, microwave-transmitting means one of whose ends is coupled to a microwave-generating device and which extends through the control section and insertion section of the endoscope and transmits microwaves generated from the microwave-generating device, and microwave-irradiating means for emitting microwaves delivered from the microwave-transmitting means in a prescribed direction. The microwave-irradiating means is coupled to the other end of the microwave-transmitting means, and provided in the insertion section of the endoscope.

DETAILED DESCRIPTION OF THE PREFERRED EMBODIMENTS

Figure 1:
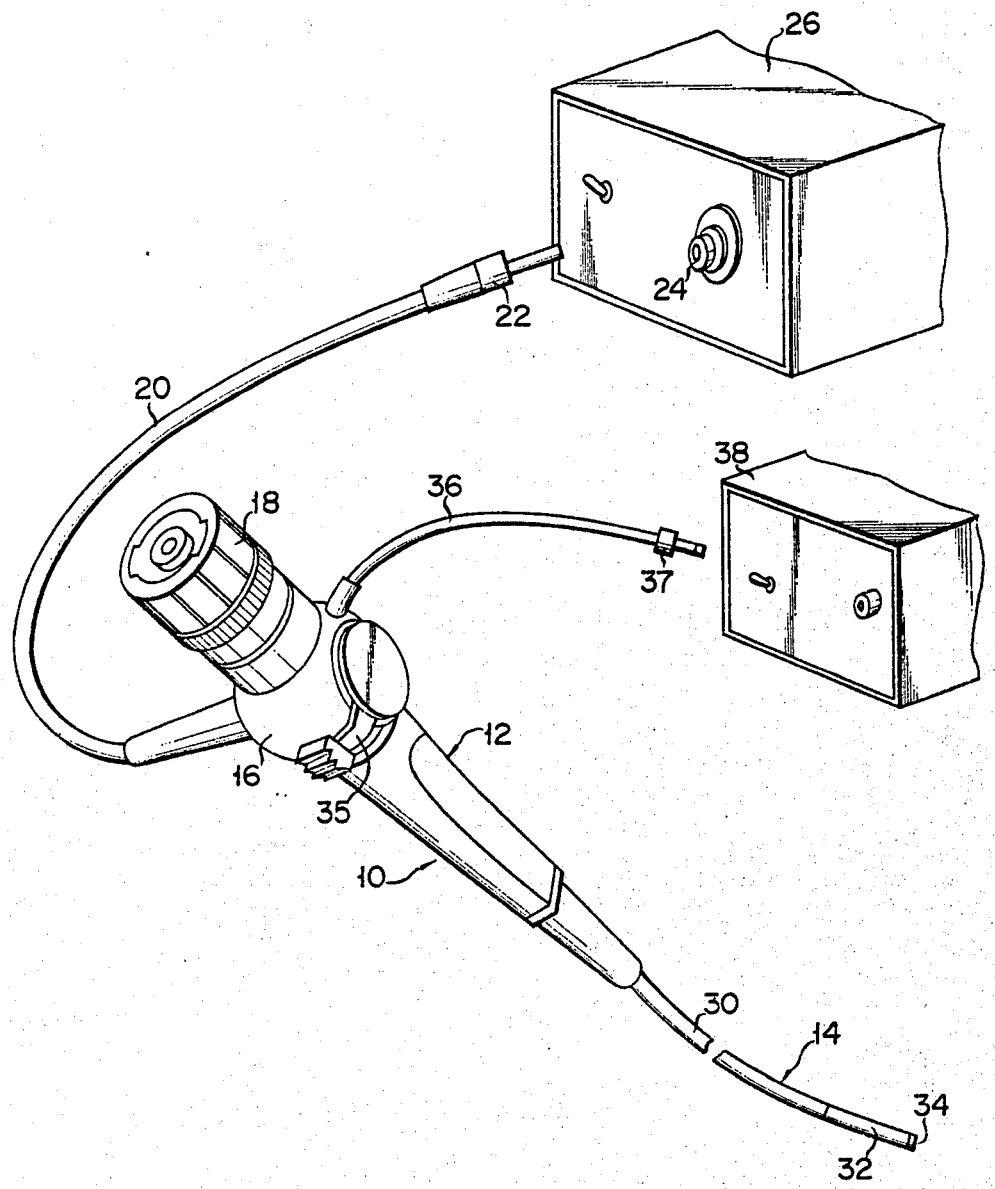
FIG. 1 is a schematic oblique view of an endoscope apparatus according to a first embodiment of this invention.
Figure 2:
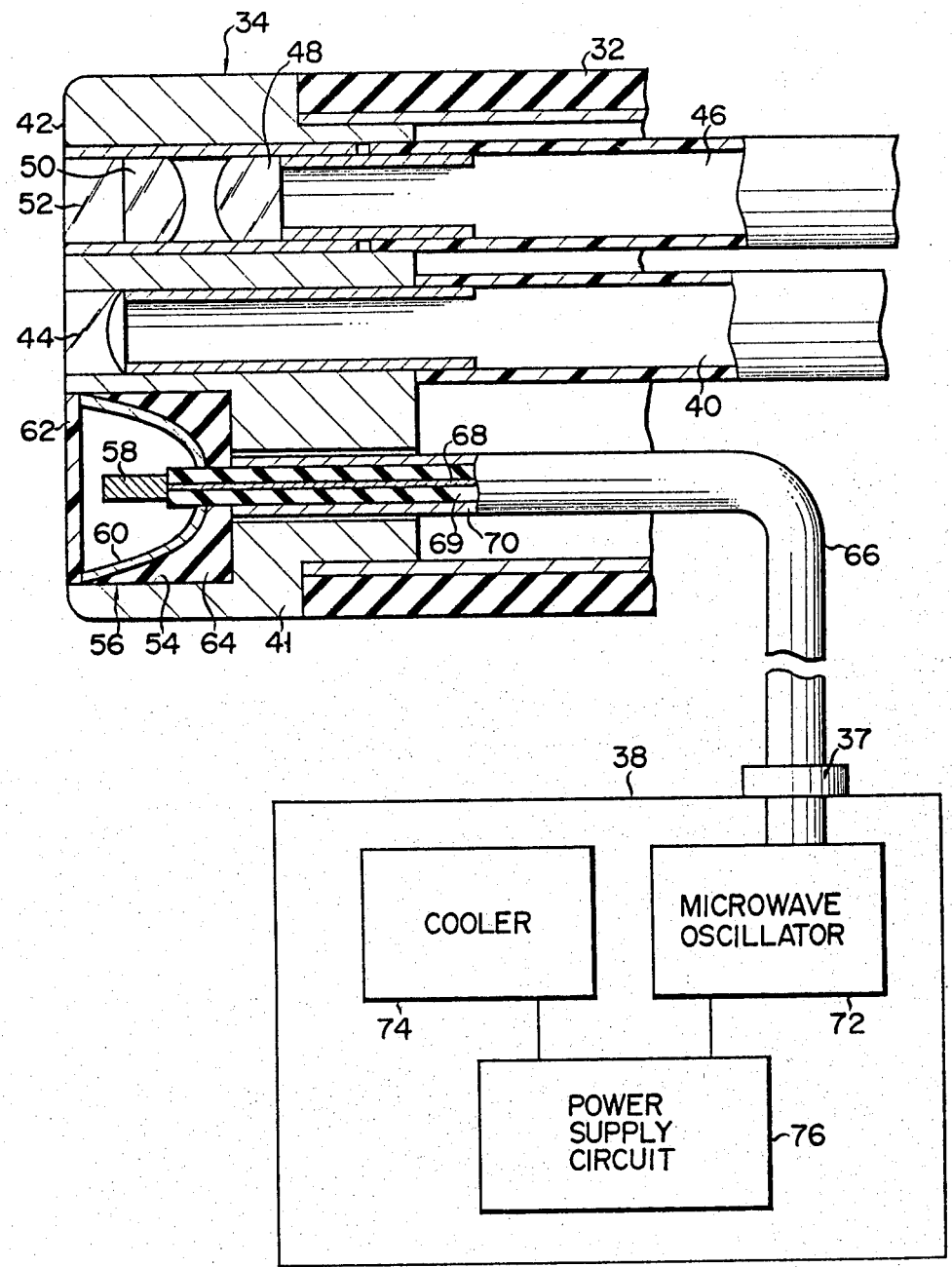
FIG. 2 is an enlarged view of the distal end portion of the endoscope apparatus of FIG. 1, also showing the arrangement of a microwave generating device attached to the endoscope apparatus.

FIGS. 1 and 2 illustrate an endoscope apparatus according to a first embodiment of this invention. As seen from FIG. 1, an endoscope apparatus 10 includes a control section 12 and insertion section 14 insertible into a coeliac cavity of a living body. An eyepiece 18 is fitted to an operation section 16 of the control section 12. A universal cord 20 extends outward from the operation section 16. The terminal end of the universal cord 20 is fitted with a connector 22. The connector 22 is detachably fitted to a socket 24 of a light source device 26. The insertion section 14 is formed of a flexible tube 30 fitted to one end of the control section 12, a bendable tube 32 connected to the flexible tube 30, and a distal end portion 34 provided at the outer end of the bendable tube 32. The outer walls of the flexible tube 30, bendable tube 32 and distal end portion 34 are made flush with each other, thereby letting all these members look as if they were formed of a single tubular member. The bendable tube 32 is connected to an angle knob 35 formed on the operation section 16 by the known means, for example, a wire. When the angle knob 35 is rotated, the bendable tube 32 can be bent in a desired extent, thereby causing the distal end portion 34 fitted to the end of the bendable tube 32 to be freely set in any direction. The distal end portion 34 is fitted with a microwave irradiator 56 shown in FIG. 2. Microwave-transmitting means, for example, wire 66 (FIG. 2) extends through the bendable tube 32, flexible tube 30 and control section 12. The microwave-transmitting wire 66 passes through a microwave-transmitting cable 36 extending outward from the operation section 16. The free end of the microwave-transmitting cable 36 is provided with a connector 37. Where the cable 36 is connected to the conventional microwave generating device 38 by means of the connector 37, then medical treatment microwaves emitted from the microwave generating device 38 are transmitted through the cable 36 to the microwave irradiator 56 (FIG. 2) provided at the distal end portion 34.

FIG. 2 illustrates the distal end portion 34 in detail. A light guide 40 is formed of a bundle of optical fibers. The light guide 40 extends from the distal end portion 34 through the insertion section 14, control section 12 and universal cord 20. When the universal cord 20 is connected to the light source device 26, then an observation light sent forth from the light source device 26 is conducted through the light guide 40 to the endoscope distal end section 34. The observation light is emitted outward through an illumination window 44, which is formed in the front wall 42 of the base 41 of the distal end portion 34. The end of an image guide 46 disposed at the endoscope distal end portion 34 is fitted with, for example, two object lenses 48, 50. An observation window 52 is formed in that part of the front wall 42 of the distal end portion 34 which faces one object lens 50. The image guide 46 extends from the endoscope distal end portion 34 to the eyepiece 18. Therefore, an image entering the observation window 52 is transmitted to the eyepiece 18 through the object lenses 48, 50 and image guide 46. The image is observed by the operator of the endoscope apparatus at the eyepiece 18.

In addition to the illumination window 44 and observation window 52, a depression 54 of, for example, the cylindrical shape is formed in the front wall 42 of the base 41 of the endoscope distal end portion 34. A microwave irradiator 56 is securely embedded in the cylindrical depression 54. The microwave irradiator 56 comprises a microwave-irradiating antenna, for example, a pole antenna 58 and a parabolic reflector 60 surrounding the pole antenna 58, which is positioned on the main axis of the parabolic reflector 60. This reflector 60 focuses microwaves emitted from the pole antenna 58 in a prescribed direction. The reflector 60 is made of metal, for example, stainless steel in order to prevent microwaves sent forth from the pole antenna 58 from scattering. A protective plate 62 is tightly fitted to the opening of the parabolic reflector 60 in order to prevent the influx of a coeliac liquid thereinto. The protective plate 62 is prepared from a material having a low dielectric property, for example, polyvinyl chloride. Provided in a space defined between the outer wall of the parabolic reflector 60 and the inner wall of the cylindrical depression 54 is an insulation member 64 in order to suppress the propagation of the radiation heat of microwaves and effect electrical insulation between the microwave irradiator 56 and the endoscope distal end portion 34. The pole antenna 58 is directly connected to the distal end of the microwave-transmitting wire 66. This wire 66 is formed of the so-called coaxial cable, and comprises a metal core 68, a surrounding insulation layer 69 and a shield 70 for covering the outer peripheral wall of the insulation layer.

The opposite (or proximal) end of the wire 66 is detachably connected to the microwave generating device 38 by means of the connector 37. Referring to FIG. 2, the microwave generating device 38 comprises a microwave oscillator 72 for emitting microwaves having a prescribed frequency of, for example, 1.6 GHz. Received in the microwave oscillator 72 are the known microwave-oscillating tube and oscillation tube output-controlling device (neither indicated). The energy of microwaves emitted from the microwave-oscillating tube is freely controlled by the oscillation tube output-controlling device. Disposed near the microwave oscillator 72 is the known cooler 74 for cooling the microwave-oscillating tube by eliminating heat released during the actuation of the microwave-oscillating tube. The microwave generating device 38 contains the known power supply circuit 76 which is connected to the microwave oscillator 72 and cooler 74 to supply them with required power. Medical treatment microwaves emitted from the oscillator 72 are transmitted through the core 68 extending through the transmission wire 66 to the pole antenna 58 provided in the microwave irradiator 56. Part of microwaves emitted from the pole antenna 58 permeates the protective plate 62 in the axial direction of the antenna 58 and goes straight outward. The remainder of the microwaves is scattered around the antenna 58 substantially in a parabolic form. Thereafter, the scattered microwaves are reflected by the reflector 60 and proceed substantially in parallel with the axis of the antenna 58, and permeate the protective plate 62 and are carried straight outward.

Description is now given of the operation of an endoscope apparatus according to the first embodiment of this invention which is arranged as described above.

The connector 22 of the universal cord 20 is first connected to the light source device 26, and then the connector 37 of the microwave-transmitting cable 36 is coupled to the microwave generating device 38. When the main switch of the light source device 26 is rendered conducting, then an illumination or observation light is transmitted to the endoscope distal end portion 34. The endoscope insertion section 14 is brought into the coeliac cavity of a patient suffering from a tumor. An operator, for example, a physician searches for the tumor by observing the coeliac cavity through the eyepiece 18. At this time, an observation light sentforth from the light source device 26 is transmitted to the distal end portion 34 of the insertion section 14 through the light guide 40 and irradiated on the coeliac tissue of the patient through the observation window 44. Reflections from the coeliac tissue are carried through the observation window 52, object lenses 50, 48 and image guide 46 to the eyepiece 18 to be observed by the operator. The operator operates the angle knob 35, while observing the image of the coeliac tissue. the bendable tube 32 is properly bent in accordance with the extent to which the angle knob 35 is operated. As a result, the distal end portion 34 fitted to the bendable tube 32 is directed to any part of the coeliac cavity by the operator.

Where a tumor is discovered in the coeliac cavity by the above-mentioned operation, then the microwave irradiator 56 is directed to the tumor. At this time, the main switch of the microwave-generating device 38 is rendered conducting, causing the microwave-generating device 38 to emit medical treatment microwaves having a prescribed radiation energy. The microwaves are transmitted to the pole antenna 58 through the transmission wire 66. Part of the microwaves emitted from the antenna 58 permeates the protective plate 62 and is sent forth outward. The remainder of the microwaves is reflected by the reflector 60 and passes through the protective plate 62 to the outside in parallel with a prescribed direction, for example, the axis of the antenna 58. Microwaves emitted from the irradiator 56 proceed through the patient's coeliac cavity, for example to the tumor. The tumor exposed to the microwaves is thermally exterminated. The microwaves having high permeability easily and reliably destroys not only a tumor grown on the surface of the coeliac tissue but also that produced in the coeliac tissue or in the deep portion of the coeliac cavity by application of heat. Unlike the energy of high frequency or laser beams, the energy of microwaves emitted from the microwave-oscillating tube can be controlled easily and continuously. Therefore, the energy of microwaves can be controlled by the known process, for example, by the aforesaid device for controlling an output from the microwave-irradiating tube to such extent as saves the normal coeliac tissue surrounding a tumor from extermination. With the apparatus of this invention, therefore, proper application of microwaves can thermally eliminate only a tumor, and reliably saves a normal coeliac tissue surrounding the tumor from damage or extermination, thereby assuring the extremely safe medical treatment of a patient's tumor.

Figure 3:
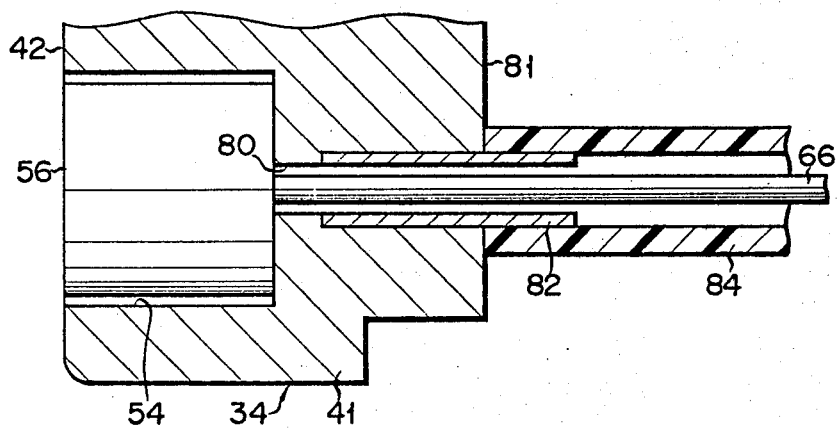
FIG. 3 is an enlarged sectional view of part of the distal end portion of an endoscope apparatus according to a second embodiment of the invention.

Description is now given with reference to FIG. 3 of an endoscope apparatus according to a second embodiment of this invention. A depression 54 of, for example, a cylindrical shape is formed in the front wall 42 of the base 41 of the endoscope distal end portion 34. The cylindrical depression 54 is chosen to have a larger inner diameter than the outer diameter of the microwave irradiator 56 placed in the depression 54, producing a gap between both members 54, 56. A passage 80 is formed through the base 41 to be connected to the substantially central part of the bottom wall of the cylindrical depression 54. The passage 80 is chosen to have a larger inner diameter than the outer diameter of the microwave-transmitting wire 66 extending through the passage 80. Part of the passage 80 is defined by the inner wall of a metal tube 82 embedded in the base 41 in airtightness. The inner wall of that portion of the passage 80 which is not defined by the inner wall of the metal tube 82 is made flush with that of the metal tube 82. The other portion of the metal tube 82 than that thereof which is embedded in the base 41 projects from the base 41. A hollow flexible cable 84 is fitted in airtightness around the outer peripheral wall of the above-mentioned other portion of the metal tube 82. In other words, the hollow flexible tube 84 is chosen to have an inner diameter substantially equal to the outer diameter of the metal tube 82. One end (the distal end) of the hollow flexible cable 84 is fixed in airtightness to the rear end wall 81 to the base 41.

With an endoscope apparatus according to the second embodiment illustrated in FIG. 3, the microwave irradiator 56 and microwave-transmitting wire 66 connected thereto are loosely inserted into the cylindrical depression 54 formed in the base 41, passage 80 and hollow flexible cable 84. Therefore, the push and pull of the microwave-transmitting wire 66 in the axial direction of the hollow flexible cable 84 enables the microwave irradiator 56 to freely protrude from or retract into the base 41 of the endoscope distal end section 34. Where the endoscope insertion section 14 (FIG. 1) is inserted into the coeliac cavity of a patient with a tumor, the operator of the endoscope, for example, a physician pushes the microwave-transmitting wire 66 to a desired extent. As a result, the microwave irradiator 56 projects from the endoscope distal end section 34, causing the front wall of the microwave irradiator 56 to be tightly attached to the surface of the living tissue of the coeliac cavity. Consequently, the loss of propagation of the microwave energy, through the air in the coeliac cavity, which is emitted from the irradiator 56 can be decreased. The endoscope operator can accurately recognize the intensity of microwave energy actually brought into the living tissue of the coeliac cavity from the irradiator 56, since the microwaves emitted from the irradiator 56 are directly introduced into the living tissue of the coeliac cavity without interposing the air in the coeliac cavity. In other words, the endoscope operator can correctly determine the required level of the intensity of microwave energy. This means that the normal living tissue other than that affected by the tumor can be more reliably prevented from being damaged or exterminated by microwaves having a higher energy than required, which might otherwise be emitted by mistake. Further, the microwave irradiator 56 which projects from the base 41 of the endoscope distal end portion 34 assures an increase in the area of the outer surface of the microwave irradiator 56 contacted by air, leading to the noticeable elevation of the heating effect of the microwave irradiator 56. In other words, the endoscope distal end portion 34 can be prevented from being adversely affected by heat generated during the actuation of the microwave irradiator 56. After the microwave irradiator 56 and microwave-transmitting wire 66 are removed from the endoscope apparatus, the depression 54, the passage 80 and the hollow section of the flexible cable 84 which are now left vacant can be applied as a passage for the insertion of a medical treatment implement, for example, forceps, thereby increasing the utility of an endoscope apparatus. Where the microwave irradiator 56 projects from the base 41 and a coeliac liquid, for example, a gastric juice or water is brought into the depression 54 of the base 41, then the metal tube 82 and hollow flexible cable 84 covering the microwave-transmitting wire 66 connected to the microwave irradiator 56 prevent the above-mentioned liquids from being undesirably carried into the endoscope apparatus.

Figure 4:
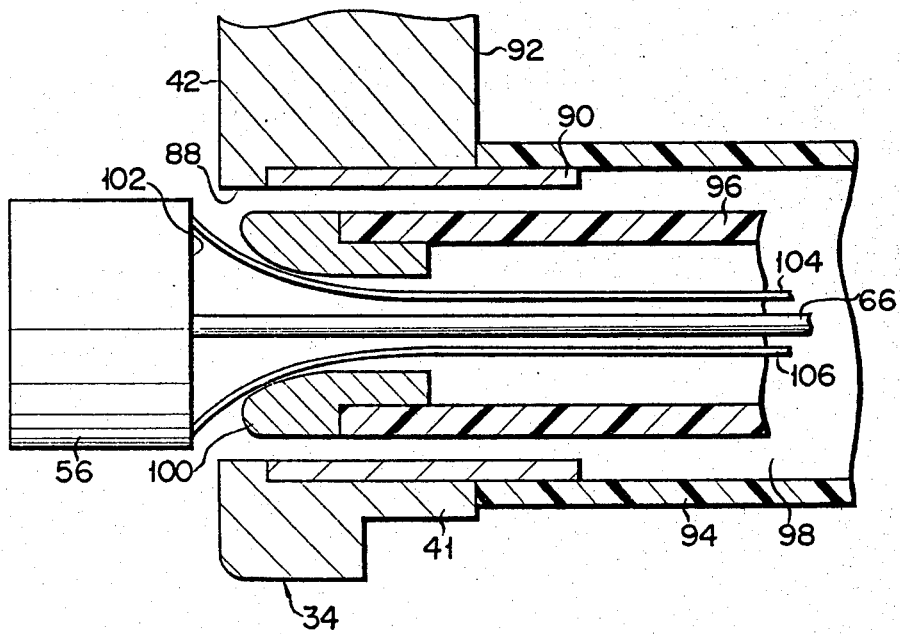
FIG. 4 is an enlarged sectional view of part of the distal end portion of an endoscope apparatus according to a third embodiment of the invention.

Description is now given with reference to FIG. 4 of an endoscope apparatus according to a third embodiment of this invention. A cylindrical cavity 88 is formed in the base 41 of the endoscope distal end portion 34. Part of the cylindrical cavity is defined by the inner wall of a metal tube 90 securely embedded in the base 41. The inner wall of the cylindrical cavity 88 defined by the base 41 itself and the inner wall of the metal tube 90 are made flush with each other. Part of the metal tube 90 projects from the rear wall 92 of the base 41. One end of a flexible cable 94 is tightly fixed to the rear wall 92 of the base 41 in airtightness. The inner surface of the proximity of said one end of the flexible cable 94 is tightly fitted in airtightness to the outer surface of that portion of the metal tube 90 which projects from the base 41. The cylindrical cavity 88 formed in the base 41 is chosen to have a larger inner diameter than the outer diameter of the microwave irradiator 56. A cylindrical flexible sheath 96 extends through the cylindrical cavity 88, metal tube 90 and hollow flexible cable 94. The cylindrical sheath 96 is chosen to have an outer diameter smaller than the inner diameter of the cylindrical cavity 88. A prescribed clearance is retained between the outer wall of the cylindrical sheath 96 and the inner wall of a sheath passage 98 defined by the cylindrical cavity 88, metal tube 90 and hollow flexible cable 94. Therefore, the cylindrical sheath 96 can freely rotate and reciprocate in the passage 98. The terminal end of the sheath 96 is fitted with a hollow round tip member 100 prepared from a wear-resistant material, for example, metal, ceramic or resin. The outer surface of the tip member 100 is made flush with that of the sheath 96. At least the inner end portion of, for example, the tip member 100 is smoothly rounded. The inner diameter of the tip member 100 is chosen to progressively decrease toward the interior of the cylindrical sheath 96 and later retaining a prescribed measurement. The microwave-transmitting wire 66 connected to the rear end of the microwave irradiator 56 extends through the hollow sheath 96. A plurality of, for example two, operation wires 104, 106 are fitted to the symmetrical points on the periphery of the rear end wall 102 of microwave irradiator 56. A distance between the ends of the operation wires 104, 106 fitted to the rear end wall 102 of the microwave irradiator 56 is chosen to be larger than the prescribed inner diameter of the tip member 100 mounted on the inner wall of the sheath 96. Where the operation wires 104, 106 and microwave-transmitting wire 66 are inserted into the sheath 96, then part of the surface of the operation wires 104, 106 contacts part of the inner wall of the end portion of the tip member 100. The operation wires 104, 106 are separately pushed and pulled by the endoscope operator, for example, a physician. Since the microwave-transmitting wire 66 is flexible, the microwave irradiator 56 can swing freely when the endoscope operator pushes or pulls the operation wires 104, 106. The microwave irradiator 56 has a smaller outer diameter than that of the cylindrical cavity 88 of the base 41. When, therefore, pulled toward the endoscope operator, the microwave-transmitting wire 66 connected to the microwave irradiator 56 causes the irradiator 56 to retract into the sheath passage 98.

Description is now given of the operation and application of an endoscope apparatus according to the third embodiment of this invention illustrated in FIG. 4. Where the endoscope insertion section 14 (FIG. 1) is drawn into a patient's coeliac cavity, then the microwave-transmitting wire 66 and sheath 96 pulled by the endoscope operator causes the microwave irradiator 56 to retract into the cylindrical cavity 88 formed in the base 41 of the endoscope distal end portion 34 and metal tube 90. Where a tumor grown in the patient's coeliac cavity is detected, then the endoscope operator pushes the microwave irradiator 56 through the cylindrical cavity 88 and moves the irradiator 56 out of the endoscope distal end portion 34. Where, at this time, either or both of the operation wires 104, 106 are actuated, then the microwave irradiator 56 can freely swing and be directed to any part of the patient's coeliac cavity as the endoscope operator wishes. Therefore, microwaves can be emitted from the irradiator 56 reliably and exactly on a tumor to be medically treated, no matter where said tumor is grown in the living tissue of the coeliac cavity. Therefore, it is possible to prominently reduce the possibility of a normal tissue surrounding the tissue affected by a tumor being exposed by mistake to microwaves and limit an amount of microwaves emitted from the irradiator 56 to the least possible extent. Consequently, microwave medical treatment is effected with safety and high efficiency. Further, if desired, the microwave irradiator 56 and sheath 96 can be rotated in an inclined state by actuating either or both of the operation wires 104, 106. At this time, microwaves can be quickly emitted from the irradiator over a broad region of the coeliac living tissue in which a tumor is produced, thereby assuring the quick and effective thermal treatment of the tumor.

Figure 5:
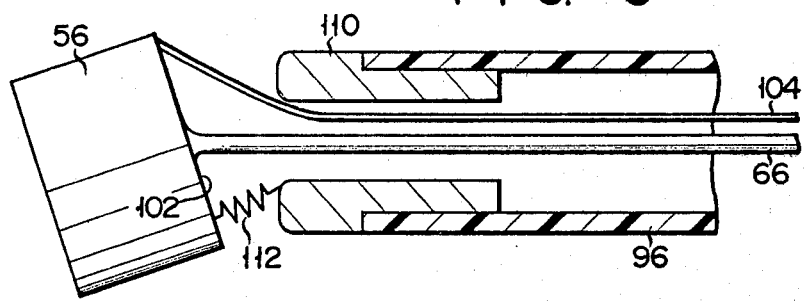
FIG. 5 indicates the sheath and microwave-irradiating device of an endoscope apparatus according to a fourth embodiment of the invention.

Description is now given with reference to FIG. 5 of an endoscope apparatus according to a fourth embodiment of this invention. A tip member 110 is fixed to that end of a sheath 96 which faces a microwave irradiator 56 having, for example, a round cylindrical shape. The tip member 110 is shaped substantially like a cylinder. The outer peripheral wall of the tip member 110 and that of the sheath 96 are made flush with each other. The tip member 110 is chosen to define a substantially cylindrical hollow space interior thereof. That end of the tip member 110 which faces the rear wall of the mirowave irradiator 56 is chamfered or rounded. The tip member 110 is chosen to have a smaller inner diameter than the outer diameter of the microwave irradiator 56. A microwave-transmitting wire 66 connected to the rear wall of the microwave irradiator 56 extends through the tip member 110 and sheath 96. One end of the tip member 110 is connected to one peripheral portion of the rear wall 102 of the microwave irradiator 56 by means of an elastic member, for example, a compression coil spring 112. A single operation wire 104 is fixed to another peripheral portion of the rear wall 102 of the microwave irradiator 56. The operation wire 104 extends through the tip member 110 and sheath 96, and is pushed or pulled by an operation knob (not shown) mounted on the endoscope body. The point on the peripheral wall 102 of the microwave irradiator 56 at which one end of the operation wire 104 is fixed is symmetric with the point on the peripheral wall 102 at which, for example, the spring 112 is set with respect to the end of the microwave-transmitting wire 66. Therefore, the microwave irradiator 56 can easily swing over a broad range by actuating the single operation wire 104.

Figure 6:
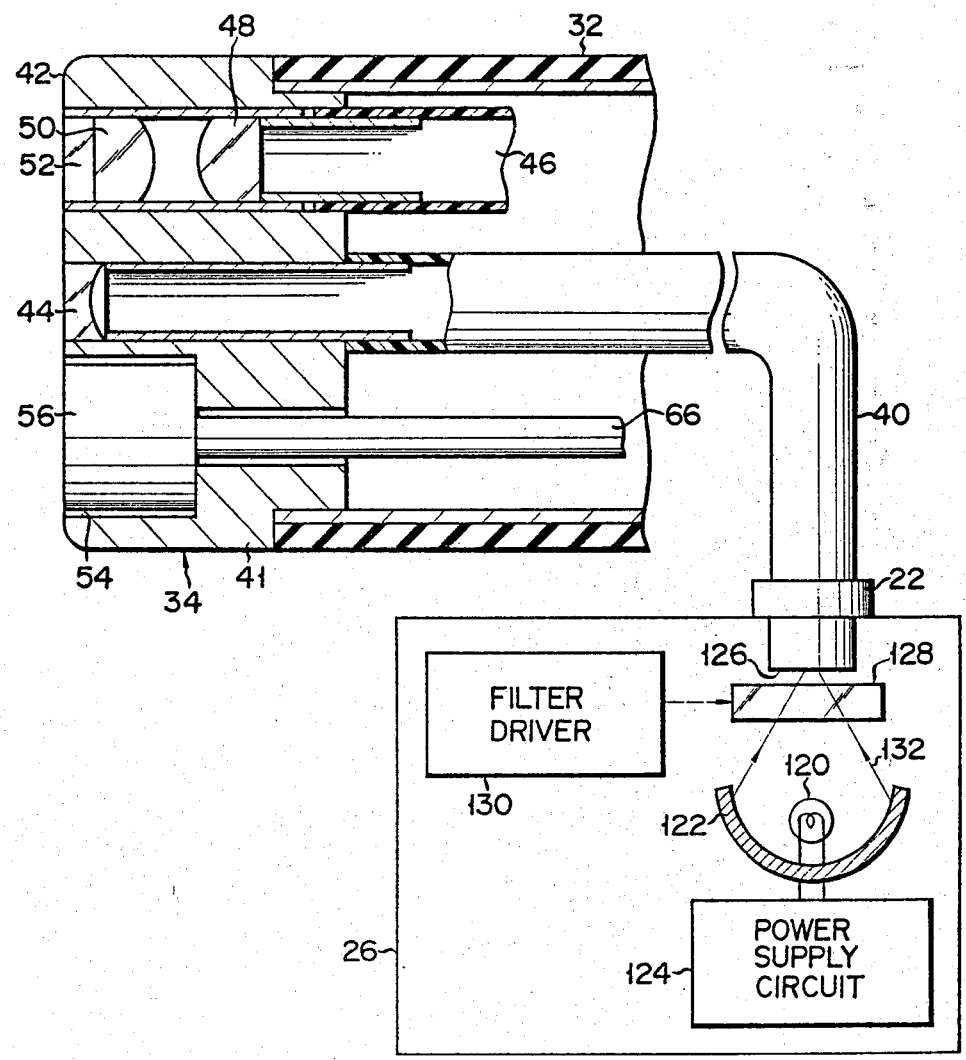
FIG. 6 is an enlarged sectional view of the distal end portion of an endoscope apparatus according to a fifth embodiment of the invention, also showing the arrangement of part of a light source device attached to the endoscope apparatus.

Description is now given with reference to FIG. 6 of an endoscope apparatus according to a fifth embodiment of this invention.

The parts of FIG. 6 the same as those of FIG. 2 are designated by the same numerals, description thereof being omitted. A connector 22 of a light guide 40 extending from the endoscope distal end portion 34 is coupled to a light source device 26, in which a lamp 120 is placed. A reflector 122 surrounds the lamp 120 connected to the known power supply circuit 124. A filter 128 permeable to electromagnetic waves having a frequency of, for example 400 nm is provided between the lamp 120 and the end face 126 of an image guide 40. The filter 128 is coupled to a filter driver 130 comprising a motor (not shown). This filter driver 130 causes the filter 128 to freely project into a light path 132. Where the filter 128 is set crosswise of the light path 132, then light beams emitted directly from the lamp 120 and reflections returning from the reflector 122 are projected on the filter 128. At this time, only the electromagnetic wave component of a light which has a frequency of about 400 nm is allowed to pass through the filter 128. The remainder of the light is obstructed by the filter 128.

Where, for example, a tumor is medically treated by an endoscope apparatus and light source device 26 arranged as described above, then a derivative of hematoporphyrin (fluorescent agent) is taken into the body of a tumor patient. The derivative of hematoporphyrin settles on a tumor grown in the living tissue of a patient. An endoscope operator, for example, a physician actuates the filter driver 130 provided in the light source device 26, causing the filter 128 to be removed from the light path 132. As a result, a light beam sent forth from the lamp 120 is carried directly into the light guide 40, and transmitted to the coeliac cavity of the tumor patient through the light guide 40, endoscope distal end portion 34 and illumination window 44. Reflections from the coeliac cavity are conducted to the eyepiece 18 (FIG. 1) through the image guide 46, and observed by the endoscope operator as an optical image. The operator operates the angle knob 35, etc., while looking at the optical image, and draws the microwave irradiator 56 near a tumor to be medically treated. When the endoscope operator pushes the microwave-transmitting line 66 connected to the microwave irradiator 56, then the irradiator 56 projects from the base 41 of the endoscope distal end portion 34. Where the operator actuates the filter driver 130 of the light source device 26, then the filter 128 is brought into the light path 132. As a result, light beams from the lamp 120 are converted into electromagnetic waves having a wave length of about 400 nm (395 to 420 nm). The converted electromagnetic waves are transmitted to the interior of the patient's coeliac cavity through the light guide 40. Where the electromagnetic waves are projected on a tumor in which the aforementioned fluorescent agent formed of, for example, hematoporphyrin, is settled, then the tumor emits a red fluorescent light having a wave length of about 620 to 700 nm. The endoscope operator can detect the position of a tumor to be medically treated very accurately by observing the red fluorescent light at the eyepiece 18. Therefore, it is possible to reduce the possibility of the normal living tissue around the tumor being exposed to microwaves by mistake and assure the greater safety of the patient's body in microwave medical treatment.

Although the present invention has been shown and described with respect to particular embodiments, various changes and modifications which are obvious to a person skilled in the art to which the invention pertains are deemed to lie within the spirit, scope, and contemplation of the invention. With the third embodiment of the invention shown in FIG. 4, the microwave irradiator 56 was provided with two operation wires. However, it is possible to change the kind and number the operation wires in accordance with the application to which the endoscope apparatus is put. For instance, where a single operation wire is fitted, for example, to the periphery of the rear wall 102 of the microwave irradiator 56, then the microwave irradiator 56 can be inclined due to a simplified arrangement. Further, actuation of three operation wires equidistantly arranged on the periphery of the rear wall 102 of the microwave irradiator 56 enables said irradiator 56 to be directed to any part of the coeliac cavity of a patient.

The filter 128 provided in the light source device 26 of the fifth embodiment shown in FIG. 6 may be formed of the so-called sharp cut filter obstructing only incoming light components having a higher wave length than 420 nm.

What is claimed is:

1. An endoscope comprising:
   an endoscope control section manually operable by an operator;
   a flexible insertion section coupled to said endoscope control section, for insertion into a coeliac cavity, said insertion section comprising a distal end portion having a distal end surface and directable in a desired direction within a prescribed range in accordance with the flexibility of said insertion section; and a passage interior of said insertion section, said passage having a prescribed inner diameter and extending lengthwise in said insertion section;
   a hollow and flexible sheath member received in said passage and having a distal end, an inner diameter and an outer diameter smaller than said inner diameter of said passage, said sheath member being reciprocatable and rotatable in said passage in accordance with an operation of said operator;
   a hollow, substantially round tip member mounted to said sheath member at said distal end of said sheath member and having an inner diameter smaller than said inner diameter of said sheath member, the outer surface of said tip member being substantially flush with the outer surface of said sheath member;
   a microwave-irradiator having a rear wall and connected at said rear wall thereof to microwave-transmitting wire, said a microwave-irradiator having an outer diameter smaller than said inner diameter of said passage so as to be selectively receivable in said passage, and having a microwave irradiation surface for irradiating microwaves outward, said microwave-irradiator being swingable substantially at the connection between said microwave-irradiator and said microwave-transmitting wire so that said microwave irradiation surface of said microwave-irradiator is directable in a desired direction when protruded out from said insertion section; and
   drive means operable by an operator and extending with said microwave-transmitting wire through said sheath member and through said tip member, said drive means being coupled to said rear wall of said microwave-irradiator for driving said microwave-irradiator to selectively cause said microwave-irradiator to protrude from or be received in said passage of said insertion section; and to swing said microwave irradiation surface in a desired direction after said microwave-irradiation is protruded from said passage in accordance with an operation of said operator.

2. The endoscope of claim 1, wherein said drive means comprises two operation wires extending through said sheath member and coupled to respective peripheral portions of said rear wall of said microwave-irradiator as to be substantially diametrically opposite to each other, whereby said microwave-irradiator is directed in a desired direction by a reciprocal motion of said operation wires when said microwave-irradiator is protruded from said insertion section.

3. The endoscope of claim 2, wherein a distance between two points on said rear wall of said microwave-irradiator to which said operation wires are respectively coupled is greater than said inner diameter of said tip member; and wherein said tip member has a rounded inner end surface, said operation wires abutting on said rounded inner end surface of said tip member when pulling force is applied to said operation wires.

4. The endoscope of claim 3, wherein said microwave-transmitting wire is coupled to a central region of said rear wall of said microwave-irradiator.

5. The endoscope of claim 4, wherein said tip member is made of wear-resistant material, preferably of one of metal, ceramic material and resin material.

6. The endoscope of claim 5, wherein said tip member is made of metal.

7. The endoscope of claim 5, wherein said tip member is made of ceramic material.

8. The endoscope of claim 5, wherein said tip member is made of resin material.

9. The endoscope of claim 1, wherein said drive means comprises:
   an operation wire extending through said sheath member and coupled to a first peripheral portion of said rear wall of said microwave-irradiator; and
   an elastic member coupled to a second peripheral portion of said rear wall of said microwave-irradiator which is substantially diametrically opposite to said first peripheral portion.

10. The endoscope of claim 9, wherein said microwave-transmitting wire is coupled to a central region of said rear wall of said microwave-irradiator.

11. The endoscope of claim 10, wherein said tip member is made of wear-resistant material.

12. The endoscope of claim 11, wherein said tip member is made of metal.

13. The endoscope of claim 11, wherein said tip member is made of ceramic material.

14. The endoscope of claim 11, wherein said tip member is made of resin material.

15. The endoscope of claim 1, wherein said microwave-irradiator comprises:

an antenna means directly connected to said microwave-transmitting wire to irradiate microwaves delivered from said microwave-transmitting wire; and reflector means surrounding said antenna means for conducting microwaves irradiated from said antenna means in a prescribed direction.

16. The endoscope of claim 15, wherein said reflector means is formed of metal, and has at least one opening facing the direction in which microwaves are brought into the reflector means from said antenna means.

17. The endoscope of claim 16, wherein said microwave-irradiator includes a protective plate made of a material having a low dielectric constant and which is fitted to an opening of said reflector means.

18. The endoscope of claim 16, wherein at least that portion of said reflector means which faces said antenna means has a parabolic shape.

19. The endoscope of claim 16, wherein said microwave-transmitting wire comprises a transmission cable which includes a core directly connected to said antenna means for transmission of microwaves.

20. The endoscope of claim 1, further comprising:

an eyepiece section coupled to said operation section;

light guide means extending through a portion of said insertion section other than said passage, for receiving a light and irradiating said light outward from said distal end portion of said insertion section; and image guide means extending through a portion of said insertion section other than said passage, for receiving an external image light from said distal end portion of said insertion section and transmitting said external image light to said eyepiece section, whereby the operator can carry out a microwave-heating treatment on an affected portion inside said coeliac cavity while observing an image inside said coeliac cavity through said eyepiece section.

* * * * *